United States Patent
Lindgren et al.

(10) Patent No.: US 9,429,484 B2
(45) Date of Patent: Aug. 30, 2016

(54) DETERMINING THE HEAT FLOW EMANATING FROM A HEAT TRANSPORTING FLUID

(75) Inventors: Mats Lindgren, Södra Sunderbyn (SE); Carl Carlander, Luleå (SE); Philip Holoch, Neschwil (CH)

(73) Assignee: BELIMO Holding AG, Hinwill (CH)

( * ) Notice: Subject to any disclaimer, the term of this patent is extended or adjusted under 35 U.S.C. 154(b) by 589 days.

(21) Appl. No.: 13/881,275

(22) PCT Filed: Oct. 19, 2011

(86) PCT No.: PCT/CH2011/000248
§ 371 (c)(1),
(2), (4) Date: Jun. 7, 2013

(87) PCT Pub. No.: WO2012/065276
PCT Pub. Date: May 24, 2012

(65) Prior Publication Data
US 2013/0259083 A1    Oct. 3, 2013

(30) Foreign Application Priority Data

Nov. 18, 2010 (CH) ................................ 1935/10

(51) Int. Cl.
G01K 17/00 (2006.01)
G01K 17/06 (2006.01)
G01K 17/10 (2006.01)
G01K 17/08 (2006.01)

(52) U.S. Cl.
CPC ............. *G01K 17/10* (2013.01); *G01K 17/08* (2013.01)

(58) Field of Classification Search
CPC combination set(s) only.
See application file for complete search history.

(56) References Cited

U.S. PATENT DOCUMENTS

| 4,440,507 | A | 4/1984 | Karras et al. |
| 5,902,043 | A * | 5/1999 | Price ................ G01K 17/08 374/1 |
| 6,823,743 | B2 * | 11/2004 | Sato .................. G01N 7/00 73/204.11 |
| 7,228,728 | B2 | 6/2007 | Ouriev et al. |
| 7,399,118 | B2 * | 7/2008 | Matter .............. G01F 1/6965 374/31 |
| 7,588,368 | B2 * | 9/2009 | Hagen ............ F02D 41/1445 374/135 |
| 2005/0204811 | A1 * | 9/2005 | Neff ................... A61B 5/00 73/204.11 |

FOREIGN PATENT DOCUMENTS

CN    1662793 A    8/2005
(Continued)

OTHER PUBLICATIONS

English Translation, Manfred (EP 1975582, applicant submitted).*
(Continued)

*Primary Examiner* — Lisa Caputo
*Assistant Examiner* — Nasir U Ahmed
(74) *Attorney, Agent, or Firm* — Sughrue Mion, PLLC

(57) ABSTRACT

The invention relates to a method for determining the heat flow (dQ/dt) emanating from a heat transporting fluid (12), which is a mixture of at least two different fluids, and which flows through a flow space (11) from a first position, where it has a first temperature (T1), to a second position, where it has, due to that heat flow (dQ/dt), a second temperature (T2), which is lower than said first temperature (T1), whereby the density and specific heat of said heat transporting fluid (12) is determined by measuring the speed of sound (vs) in said fluid, and said density and specific heat of said heat transporting fluid (12) is used to determine the heat flow (dQ/dt).

20 Claims, 2 Drawing Sheets

(56) References Cited

FOREIGN PATENT DOCUMENTS

| DE | 197 39 367 A1 | 7/1999 |
| DE | 10 2005 043699 A1 | 3/2007 |
| EP | 1 975 582 A2 | 10/2008 |

OTHER PUBLICATIONS

English Translation of Foreign Reference (EP1975582), Oct. 1, 2008.*
International Search Report for PCT/CH2011/000248 dated Feb. 3, 2012.

* cited by examiner

DETERMINING THE HEAT FLOW EMANATING FROM A HEAT TRANSPORTING FLUID

CROSS REFERENCE TO RELATED APPLICATIONS

This application is a National Stage of International Application No. PCT/CH2011/000248 filed Oct. 19, 2011, claiming priority based on Swiss Patent Application No. 1935/10 filed Nov. 18, 2010, the contents of all of which are incorporated herein by reference in their entirety.

BACKGROUND OF THE INVENTION

The present invention relates to the technology of measuring thermal quantities. It refers to a method for determining the heat flow emanating from a heat transporting fluid according to the preamble of claim 1.

PRIOR ART

Binary mixtures of two fluids are often used in terminal systems, especially related to heating, cooling or air conditioning etc. A well-known binary fluid is a water/antifreeze fluid mixture, especially in form of a water/glycol mixture. When such a mixture or binary fluid transports heat energy and delivers this energy at a point of the circulating liquid system, it is necessary to know the actual mixing ratio of the heat transporting fluid, when the energy delivered shall be calculated from certain measurements at the system.

Unfortunately, the mixing ratio of such a binary liquid or other fluid mixtures changes with time, as, for example, water can evaporate from the system, or water is refilled, thereby changing the mixing ratio.

Document DE 102005043699 discloses a sensing unit for a vehicle, which determines the content of an anticorrosion medium in the fluid system of the vehicle. To determine the mixing ratio, the speed of sound is measured within the fluid.

Document DE 19533927 combines the capacity measurement and a measurement of the speed of sound to determine and control the concentration of a washing detergent within a cleaning fluid.

Document DE 3741577 discloses a method and system for measuring the mixing ratio of a binary fluid by leading a microwave signal through said liquid.

The cited documents are silent with respect to the determination of the heat flow emanating from a heat transporting fluid, which is a mixture of different fluids.

SUMMARY OF THE INVENTION

It is an object of the invention to provide a method for determining the heat flow emanating from a heat transporting fluid, which is a mixture of different fluids.

It is a further object of the invention to provide a heat flow measuring arrangement for carrying out said method.

These and other objects are obtained by a method according to claim 1 and heat flow measuring arrangement according to claim 13.

The method according to the invention comprises the steps of:
a) measuring the differential temperature between said first temperature and said second temperature;
b) measuring the speed of sound within said heat transporting fluid at a predetermined location of said flow space in the vicinity of said first and/or second position;
c) measuring the absolute temperature of the heat transporting fluid at said predetermined location;
d) measuring the volume flow at said predetermined location;
e) determining from said measured absolute temperature and said measured speed of sound the mixing ratio of said heat transporting fluid;
f) determining from said measured absolute temperature and said determined mixing ratio of said heat transporting fluid the density and the specific heat of said heat transporting fluid; and
g) determining from said measured differential temperature, said measured volume flow, said determined density and said determined specific heat the heat flow emanating from said heat transporting fluid.

According to an embodiment of the inventive method said heat transporting fluid is a binary mixture of two fluids.

Especially, said heat transporting fluid is a mixture of water and an antifreeze fluid.

More specifically, said heat transporting fluid is a water/glycol mixture.

According to another embodiment of the inventive method the mixing ratio of said heat transporting fluid is determined from said measured absolute temperature and said measured speed of sound by means of a data table for the relation between speed of sound, absolute temperature and mixing ratio of the specific heat transporting fluid.

Alternatively, the mixing ratio of said heat transporting fluid may be determined from said measured absolute temperature and said measured speed of sound by means of a mathematical relation between speed of sound, absolute temperature and mixing ratio of the specific heat transporting fluid.

According to another embodiment of the invention the speed of sound within said heat transporting fluid is measured by means of an ultrasonic measuring arrangement.

More specifically, the ultrasonic measuring arrangement comprises a first ultrasonic transducer placed at a first side of said flow space and a second ultrasonic transducer placed at a second side of said flow space, such that an ultrasonic signal travelling between said first and second ultrasonic transducers passes the fluid within said flow space.

Especially, the first and second ultrasonic transducers are arranged with respect to the fluid flow within said flow space, such that an ultrasonic signal travelling between said first and second ultrasonic transducers has a velocity component in the direction of said fluid flow, the speed of sound is measured in opposite directions between said first and second ultrasonic transducers, and the volume flow is derived from the measured different speeds of sound in said opposite directions.

When a special arrangement for the measurement of the sound of speed is used, the flow velocity of the fluid may be determined from two different measurements of the speed of sound, namely in the flow direction and opposite to the flow direction. The volume flow can then be calculated from the flow velocity and the cross-sectional area of the flow space or tube. However, according to another embodiment of the invention said volume flow is measured by means of a separate flow meter.

According to another embodiment the measurement of the speed of sound is based on measuring the transit time of an ultrasonic pulse travelling between said first and second ultrasonic transducers.

More specifically, the measurement of the speed of sound is done according to the sing-around method.

The heat flow measuring arrangement according to the invention comprises:

a) first means for measuring the differential temperature between said first temperature and said second temperature;

b) second means for measuring the speed of sound within said heat transporting fluid at a predetermined location of said flow space in the vicinity of said first and/or second position;

c) third means for measuring the absolute temperature of the heat transporting fluid at said predetermined location;

d) fourth means for measuring the volume flow at said predetermined location;

whereby said first, second, third and fourth means are connected to an evaluation unit for determining said heat flow based on the data it receives from said first, second, third and fourth means.

According to an embodiment of the inventive heat flow measuring arrangement said first means for measuring the differential temperature comprises a first temperature probe placed at said first position, and a second temperature probe placed at said second position downstream of said first position.

More specifically, said second means for measuring the speed of sound within said heat transporting fluid at a predetermined location of said flow space comprises an ultrasonic measuring arrangement, which is connected to an ultrasonic control unit.

Basically, the absolute temperature can be determined from the measured first and second temperatures of the first and second temperature probes. However, according to another embodiment of the invention said third means for measuring the absolute temperature of the heat transporting fluid at said predetermined location comprises a third temperature probe, which is placed between said first and second temperature probes in the flow direction.

According to another embodiment said fourth means for measuring the volume flow at said predetermined location comprises a separate flow meter.

According to just another embodiment a data table is provided for the relation between speed of sound, absolute temperature and mixing ratio of the specific heat transporting fluid, and the evaluation unit has access to said data table.

According to another embodiment of the invention said ultrasonic measuring arrangement comprises at least two ultrasonic transducers, which are arranged, such that an ultrasonic signal travelling between said at least two ultrasonic transducers passes through said heat transporting fluid.

More specifically, said at least two ultrasonic transducers are arranged with respect to the flow direction of said heat transporting fluid, such that the measuring track between said at least two ultrasonic transducers intersects said flow direction under an oblique angle.

BRIEF DESCRIPTION OF THE DRAWINGS

The present invention is now to be explained in more detail by means of different embodiments and with reference to the attached drawings.

DETAILED DESCRIPTION OF DIFFERENT EMBODIMENTS OF THE INVENTION

Figure 1:
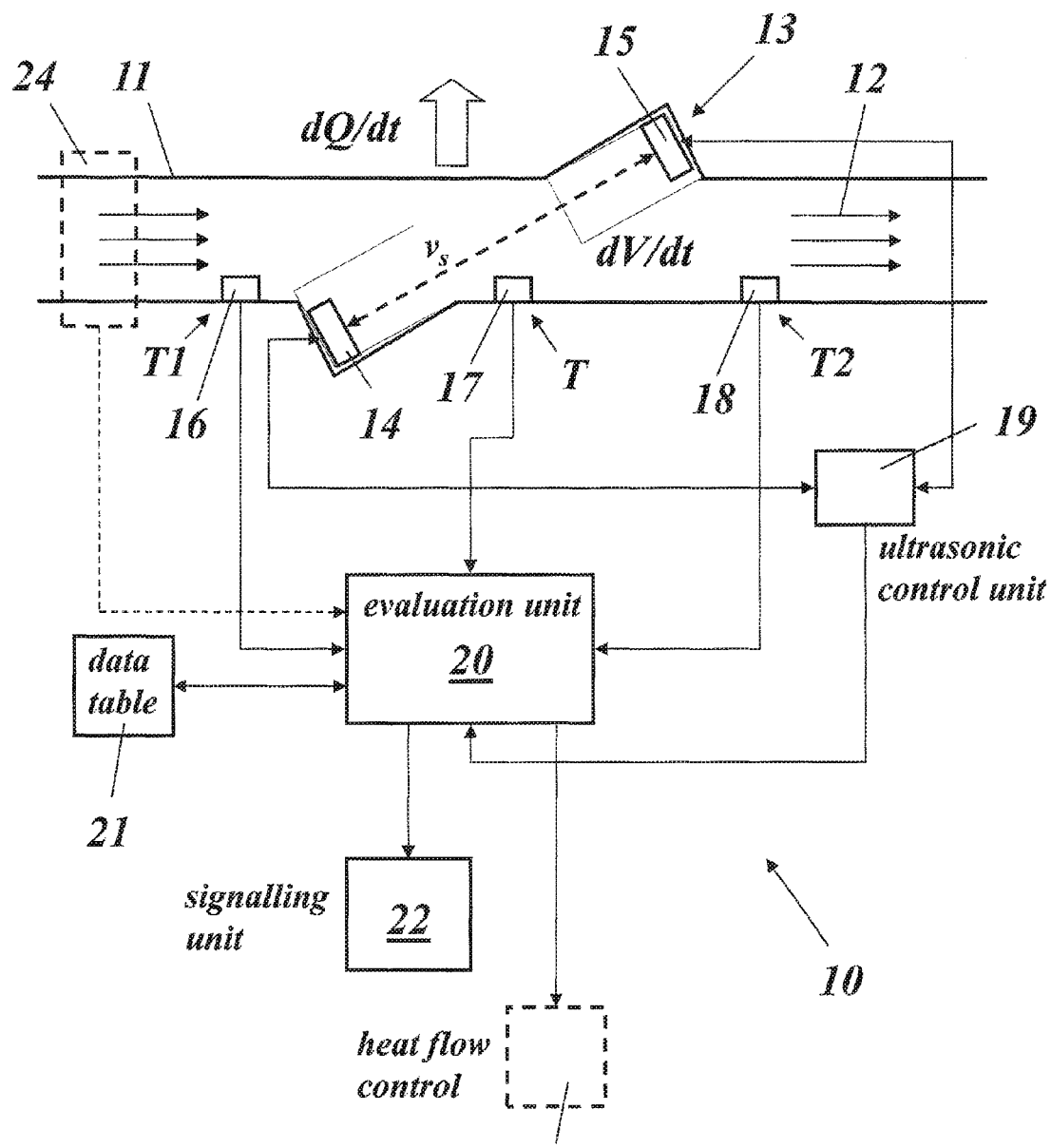
FIG. 1 shows a heat flow measuring arrangement according to an embodiment of the invention.

FIG. 1 shows a heat flow measuring arrangement 10 according to an embodiment of the present invention. Central part of the arrangement is a flow space 11, e.g. a tube. A fluid 12, especially in form of a binary fluid, more specifically a water/antifreeze fluid mixture, or even more specifically a water/glycol mixture, flows through said flow space 11 with a flow direction, which is defined by the sets of arrows in FIG. 1.

At the left side of the flow space 11 the fluid 12 has a first temperature T1, at the right side of the flow space 11 a second temperature T2, which is lower than T1. The temperature difference or differential temperature $\Delta T = T1 - T2$ is the result of a heat flow $dQ/dt$, which emanates from the fluid 12 and leaves the flow space 11 (see broad arrow in FIG. 1). The heat flow $dQ/dt$ may be caused by a heating radiator or a heat exchanger, or the like.

According to basic physical principles (see for example document U.S. Pat. No. 4,440,507) the heat flow $dQ/dt$ can be determined using the following equation:

$$dQ/dt = \dot{Q} = \rho \cdot C \cdot \dot{V}(T1 - T2) = \rho \cdot C \frac{dV}{dt} \Delta T \qquad (1)$$

$\rho$ being the density of the fluid, $\dot{V} = dV/dt$ being the volume flow of the fluid, and C being its heat capacity. The differential temperature $\Delta T$ can be easily measured by measuring the temperatures T1 and T2 at the locations given above. The volume flow $dV/dt$ can be easily determined from the flow velocity of the fluid 12 and the cross-sectional area of the flow space 11. However, the situation is different for the density $\rho$ and the heat capacity C. When the fluid 12 is a mixture of at least two different fluids, especially a mixture of water and an antifreeze fluid like glycol, which is often the case in the heating and air conditioning area, both factors depend not only on the absolute temperature, but also on the mixing ratio of the fluid 12. If the kind of antifreeze fluid and the mixing ratio are known, it is quite simple to put the correct (T-dependent) factors $\rho$ and C into the equation (1), above.

However, it is often the case, that the mixing ratio of the fluid 12 changes in time, e.g. by evaporation of water from or adding water to the system of circulating fluid, so that the factors $\rho$ and C change their value and the results of the determination of the heat flow $dQ/dt$ by means of equation (1) become wrong. Accordingly, the mixing ratio must be determined at least from time to time to make sure, that the results of a heat flow calculation are correct.

Figure 2:
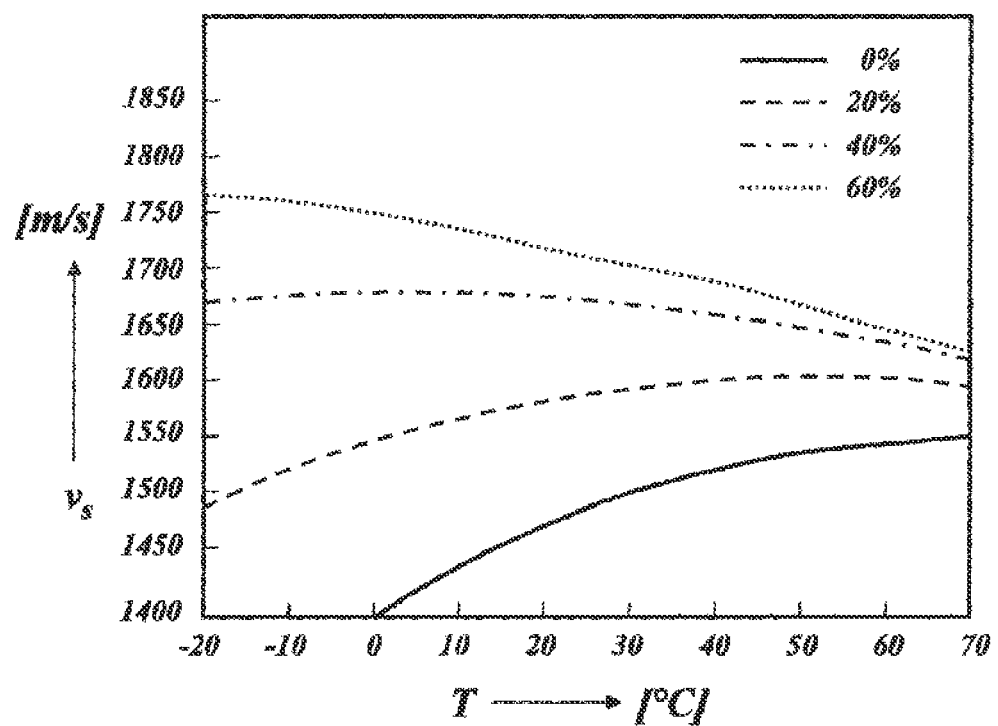
FIG. 2 shows a set of curves characteristic for the dependence of the speed of sound on temperature for a binary water/glycol mixture having a fraction of glycol of 0, 20, 40 and 60%, which can be used to determine the mixing ratio, when the speed of sound and the absolute temperature are known.

Now, it is known in the prior art (see for example document DE 10 2005 043 699, especially section [0024]), that the mixing ratio of a mixture of fluids can be determined from the speed of sound, which is measured within said mixture. When the speed of sound has been measured in such a fluid, calibration measurements or mathematical relationships between the parameters (algorithms) can be used to determine the actual mixing ratio. FIG. 2 shows a set of curves, which characterise the dependence of the speed of sound $v_s$ on temperature T for a binary water/glycol mixture having a fraction of glycol of 0, 20, 40 and 60%. Although only four exemplary curves are shown, it is clear, that for a precise determination of the mixing ratio much more curves with a very narrow distance between adjacent curves are needed.

Taking the diagram of FIG. 2, the mixing ratio can be determined by finding the point of intersection in said diagram for a given absolute temperature T and a given speed of sound $v_s$. This point of intersection lies on one of those curves, which gives the respective mixing ratio corresponding to said curve. It is clear, that such a diagram can be transformed into a data table containing discrete values of the parameters involved. Such a data table can be easily accessed by a computer to find the correct value of the mixing ratio, when the corresponding values of absolute temperature T and speed of sound $v_s$ are known.

The heat flow measuring arrangement 10 of FIG. 1 comprises an ultrasonic measuring arrangement 13, which can be used not only to measure the speed of sound $v_s$ within the fluid 12 of the flow space 11, but also to measure or determine the volume flow dV/dt of the fluid 12 flowing through the flow space 11. The ultrasonic measuring arrangement 13 comprises a first ultrasonic transducer 14 and a second ultrasonic transducer 15. Both transducers 14, 15 define a measuring track within the flow space 11, which lies with its whole length in the fluid 12. The measuring track intersects the flow direction of the fluid 12 under an oblique angle.

The ultrasonic transducers 14 and 15 are able to transmit and receive ultrasonic pulses, which travel along the measuring track. When the first transducer 14 emits an ultrasonic pulse, which is received by the second transducer 15, this pulse travels between those transducers with a downstream time t1, which can be expressed as:

$$t1 = \frac{L}{v_s + a \cdot v_f}, \quad (2)$$

where L is the length of the measuring track and (a $v_f$) is the component of the flow velocity $v_f$ of the fluid 12 parallel to the direction of the measuring track.

When the second transducer 15 emits an ultrasonic pulse, which is received by the first transducer 14, this pulse travels between those transducers with an upstream time t2, which can be expressed as:

$$t2 = \frac{L}{v_s - a \cdot v_f}. \quad (3)$$

By subtractive combination of equations (2) and (3), the speed of sound $v_s$ can be eliminated, so that the flow velocity $v_f$ of the fluid 12 is:

$$v_f = k \frac{L}{2}\left(\frac{1}{t1} - \frac{1}{t2}\right), \quad (4)$$

where the experimentally determined calibration factor k contains not only the factor a, above, but also effects connected with the non-ideal measuring situation (flow profile, side effects etc.).

From the flow velocity $v_f$ and the known cross-sectional area A of the flow space or tube 11, the volume flow dV/dt can be determined as follows:

$$\dot{V} = dV/dt = A \cdot v_f = A \cdot k \frac{L}{2}\left(\frac{1}{t1} - \frac{1}{t2}\right). \quad (5)$$

By additive combination of equations (2) and (3), the flow velocity $v_f$ can be eliminated to give the speed of sound $v_s$:

$$v_s = k' \cdot \frac{L}{2}\left(\frac{1}{t1} + \frac{1}{t2}\right) \quad (6)$$

with another calibration factor k' of the kind described before.

The precision of the determination of the speed of sound can be improved when using the so-called "sing-around" method (see for example JP 2003302270). In the heat flow measuring device 10 of FIG. 1 a sing-around loop is established by sending an ultrasonic pulse from transducer 14 to transducer 15. The pulse is received and fed back into ultrasonic control unit 19, which then excites a new ultrasonic pulse starting from transducer 14. This loop is maintained several times, and the ultrasonic control unit 19 measures the total time it takes to complete these several sing-around loops. The time it takes for the pulse to travel along the measuring track for one-time is then determined by dividing the total time by the number of loops having been run through.

Thus, the ultrasonic measuring arrangement 13 with its transducers 14 and 15 and an ultrasonic control unit 19 for controlling the transducers 14 and 15 is able to measure and to determine the speed of sound $v_s$ as well as the volume flow dV/dt within the fluid 12 and the flow space 11. However, it is also possible, to measure the volume flow dV/dt directly by means of a separate flow meter 24, which may be of a kind well-known in the art. The results of these measurements and determinations are sent to a central evaluation unit 20, which contains the computer power necessary to calculate and/or determine the actual mixing ratio of the fluid 12.

When a data table 21 is used, which is a numerical equivalent of a diagram like that shown in FIG. 2, the evaluation unit 20 takes the actual values of the speed of sound $v_s$ and the absolute temperature T and reads out from the data table 21 the corresponding value of the mixing ratio. The absolute temperature T is measured by means of a temperature probe 17 located in the vicinity of the measuring track of the ultrasonic measuring arrangement 13. Instead of using a data table 21, the mixing ratio can be evaluated by using an appropriate algorithm. Alternatively, the absolute temperature T may be determined as a mean of temperatures T1 and T2.

The mixing ratio so determined can be used in different ways. First of all, a signal can be sent out by means of an optical or acoustical signalling unit 22, which is connected to and driven by the evaluation unit 20, when the mixing ratio crosses preset limit. In case, where a minimum content of antifreeze fluid is necessary to avoid freezing of the system, e.g. on cold winter days, the signal may be sent out, when the antifreeze fluid content becomes smaller than a preset lower limit.

Furthermore, the determined or estimated mixing ratio can be used together with the measured absolute temperature T and the knowledge of the kind and parameters of the antifreeze fluid involved to determine the actual density ρ and heat capacity C of the binary fluid 12. Using equation (1)

and the measurement of the differential temperature ΔT (with temperature probes 16 and 18), the actual heat flow dQ/dt can then be evaluated.

This evaluated heat flow dQ/dt can on the one hand be integrated over time to specify the amount of thermal energy delivered from the circulating fluid system for heating cost billing purposes. On the other hand, the evaluated heat flow dQ/dt can be used to control the circulating fluid system and the delivery of thermal energy by means of a heat flow control 23, which is connected to the evaluation unit 20.

LIST OF REFERENCE NUMERALS 10 heat flow measuring arrangement
11 flow space (e.g. tube)
12 fluid (especially binary)
13 ultrasonic measuring arrangement
14,15 transducer (ultrasonic)
16,17,18 temperature probe
19 ultrasonic control unit
20 evaluation unit
21 data table
22 signalling unit
23 heat flow control
24 flow meter
T,T1,T2 temperature
ΔT differential temperature
dQ/dt heat flow
dV/dt volume flow
$v_f$ flow velocity
$v_s$ speed of sound

The invention claimed is:

1. A method for determining heat flow (dQ/dt) emanating from a heat transporting fluid (12), which is a mixture of at least two different fluids, and which flows through a flow space (11) from a first position, where said heat transporting fluid (12) has a first temperature (T1), to a second position, where said heat transporting fluid (12) has, due to said heat flow (dQ/dt), a second temperature (T2), which is lower than said first temperature (T1), said method comprising the steps of:
  a) measuring a differential temperature (ΔT) between said first temperature (T1) and said second temperature (T2);
  b) measuring a speed of sound ($v_s$) within said heat transporting fluid (12) at a predetermined location of said flow space (11) in a vicinity of said first and/or second position;
  c) measuring an absolute temperature (T) of the heat transporting fluid (12) at said predetermined location;
  d) measuring a volume flow (dV/dt) at said predetermined location;
  e) determining from said measured absolute temperature (T) and said measured speed of sound ($v_s$) a mixing ratio of said heat transporting fluid (12);
  f) determining from said measured absolute temperature (T) and said determined mixing ratio of said heat transporting fluid (12) a density and a specific heat of said heat transporting fluid (12); and
  g) determining from said measured differential temperature (ΔT), said measured volume flow (dV/dt), said determined density and said determined specific heat the heat flow (dQ/dt) emanating from said heat transporting fluid (12).

2. The method according to claim 1, characterised in that said heat transporting fluid (12) is a binary mixture of two fluids.

3. The method according to claim 2, characterised in that said heat transporting fluid (12) is a mixture of water and an antifreeze fluid.

4. The method according to claim 3, characterised in that said heat transporting fluid (12) is a water and glycol mixture.

5. The method according to claim 1, characterised in that the mixing ratio of said heat transporting fluid (12) is determined from said measured absolute temperature (T) and said measured speed of sound ($v_s$) by means of a data table (21) for the relation between speed of sound ($v_s$), absolute temperature (T) and mixing ratio of the specific heat transporting fluid (12).

6. The method according to claim 1, characterised in that the mixing ratio of said heat transporting fluid (12) is determined from said measured absolute temperature (T) and said measured speed of sound ($v_s$) by means of a mathematical relation between speed of sound ($v_s$), absolute temperature (T) and mixing ratio of the specific heat transporting fluid (12).

7. The method according to claim 1, characterised in that the speed of sound ($v_s$) within said heat transporting fluid (12) is measured by means of an ultrasonic measuring arrangement (13).

8. The method according to claim 7, characterised in that the ultrasonic measuring arrangement (13) comprises a first ultrasonic transducer (14) placed at a first side of said flow space (11) and a second ultrasonic transducer (15) is placed at a second side of said flow space (11), such that an ultrasonic signal travelling between said first and second ultrasonic transducers (14, 15) passes the fluid (12) within said flow space (11).

9. The method according to claim 8, characterised in that, the first and second ultrasonic transducers (14, 15) are arranged with respect to the fluid flow within said flow space (11), such that an ultrasonic signal travelling between said first and second ultrasonic transducers (14, 15) has a velocity component in the direction of said fluid flow, the speed of sound ($v_s$) is measured in opposite directions between said first and second ultrasonic transducers (14, 15), and the volume flow (dV/dt) is derived from the measured different speeds of sound ($v_s$) in said opposite directions.

10. The method according to claim 8, characterised in that the measurement of the speed of sound ($v_s$) is based on measuring transit time of an ultrasonic pulse travelling between said first and second ultrasonic transducers (14, 15).

11. The method according to claim 10, characterised in that the measurement of the speed of sound ($v_s$) is done according to a sing-around method.

12. The method according to claim 1, characterised in that said volume flow (dV/dt) is measured by means of a separate flow meter (24).

13. A heat flow measuring arrangement (10) for carrying out the method according to claim 1, said heat flow measuring arrangement (10) comprising:
  a) first means (16, 18) for measuring the differential temperature (ΔT) between said first temperature (T1) and said second temperature (T2);
  b) second means (13, 19) for measuring the speed of sound ($v_s$) within said heat transporting fluid (12) at a predetermined location of said flow space (11) in the vicinity of said first and/or second position;
  c) third means (17) for measuring the absolute temperature (T) of the heat transporting fluid (12) at said predetermined location;
  d) fourth means (13, 24) for measuring the volume flow (dV/dt) at said predetermined location;

whereby said first, second, third and fourth means (13, 16, 17, 18, 19, 24) are connected to an evaluation unit (20) for determining said heat flow (dQ/dt) based on the data it receives from said first, second, third and fourth means (13, 16, 17, 18, 19, 24).

14. The heat flow measuring arrangement according to claim 13, characterised in that said first means for measuring the differential temperature ($\Delta T$) comprises a first temperature probe (16) placed at said first position, and a second temperature probe (18) placed at said second position downstream of said first position.

15. The heat flow measuring arrangement according to claim 14, characterised in that said second means for measuring the speed of sound ($v_s$) within said heat transporting fluid (12) at a predetermined location of said flow space (11) comprises an ultrasonic measuring arrangement (13), which is connected to an ultrasonic control unit (19).

16. The heat flow measuring arrangement according to claim 15, characterised in that said third means for measuring the absolute temperature (T) of the heat transporting fluid (12) at said predetermined location comprises a third temperature probe (17), which is placed between said first and second temperature probes (16, 18) in the flow direction.

17. The heat flow measuring arrangement according to claim 15, characterised in that said fourth means for measuring the volume flow (dV/dt) at said predetermined location comprises a separate flow meter (24).

18. The heat flow measuring arrangement according to claim 15, characterised in that said ultrasonic measuring arrangement (13) comprises at least two ultrasonic transducers (14, 15), which are arranged, such that an ultrasonic signal travelling between said at least two ultrasonic transducers (14, 15) passes through said heat transporting fluid (12).

19. The heat flow measuring arrangement according to claim 18, characterised in that said at least two ultrasonic transducers (14, 15) are arranged with respect to the flow direction of said heat transporting fluid (12), such that a measuring track between said at least two ultrasonic transducers (14, 15) intersects said flow direction under an oblique angle.

20. The heat flow measuring arrangement according to claim 13, characterised in that a data table (21) is provided for the relation between speed of sound ($v_s$), absolute temperature (T) and mixing ratio of the specific heat transporting fluid (12), and the evaluation unit (20) has access to said data table (21).

* * * * *